United States Patent [19]
Volkmann et al.

[11] Patent Number: 4,794,179
[45] Date of Patent: Dec. 27, 1988

[54] 2-(1-OXO-3-THIOLANYL)-2-PENEM ANTIBIOTICS

[75] Inventors: Robert A. Volkmann, Ledyard; David L. Lindner, Niantic, both of Conn.

[73] Assignee: Pfizer Inc., New York, N.Y.

[21] Appl. No.: 128,375

[22] Filed: Dec. 3, 1987

Related U.S. Application Data

[60] Division of Ser. No. 877,831, Jun. 24, 1986, Pat. No. 4,739,047, which is a continuation-in-part of Ser. No. 788,273, Oct. 17, 1985, abandoned.

[51] Int. Cl.$^4$ ........................................... C02D 409/12
[52] U.S. Cl. .................................... 540/354; 548/952
[58] Field of Search ................. 540/357, 354; 548/952

[56] References Cited

U.S. PATENT DOCUMENTS 4,530,793  7/1985  Girijavallabhan et al. ......... 540/357
4,619,924 10/1986  Hamanaka ........................... 540/357

Primary Examiner—Alan L. Rotman
Assistant Examiner—Robert C. Whittenbaugh
Attorney, Agent, or Firm—Peter C. Richardson; J. Trevor Lumb; Robert K. Blackwood

[57] ABSTRACT

Process and intermediates for the conversion of 3R,4R-4-acetoxy-3-[1R-1-(silyloxy)ethyl]-2-azetidinones to antibacterial 5R,6S-6-(1R-1-hydroxyethyl)-2-(1-oxo-3-thiolanylthio)-2-penem-3-carboxylic acids, and the pharmaceutically-acceptable salts and pivaloyloxymethyl esters thereof.

7 Claims, No Drawings

2-(1-OXO-3-THIOLANYL)-2-PENEM ANTIBIOTICS

CROSS REFERENCE TO RELATED APPLICATION

This application is a division of copending application Ser. No. 877,831, filed June 24, 1986, now U.S. Pat. No. 4,739,047, which is a continuation-in-part of application Ser. No. 788,273, filed Oct. 17, 1985, now abandoned.

BACKGROUND OF THE INVENTION

The present invention concerns an improved process and intermediates for the preparation of 5R,6S-6-(1R-1-hydroxyethyl)-2-(1-oxo-3-thiolanylthio)-2-penem-3-carboxylic acids, of the formula

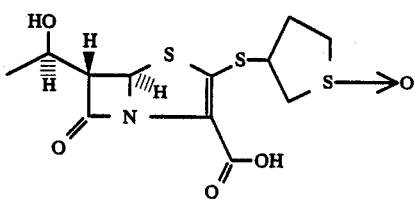
(I)

or a pharmaceutically-acceptable cationic salt or the pivaloyloxymethyl ester thereof, in particular a salt or ester which is an approximately 1:1 mixture of diastereoisomers in which the penem 2-substituent is (cis-1-oxo-3-thiolanylthio), i.e., the thiolane ring substituents are cis relative to each other. These compounds were first described in European Patent Application No. 130025, which further discloses the method of using these compounds as antibacterial agents.

The method of synthesis disclosed in EP No. 130025 is highly versatile, permitting the facile synthesis of a wide variety of analogs. However, for individual compounds, particularly the above preferred cis compound and its pivaloyloxymethyl ester, a more direct synthesis comprising fewer chemical steps is highly desirable.

SUMMARY OF THE INVENTION

An attractive precursor for the above compounds of the formula (I) is 3R,4R-4-acetoxy-3-[1R-1-(dimethyl-t-butylsilyloxy)ethyl]-2-azetidinone, of the formula

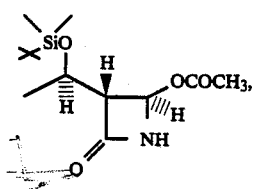
(A)

a compound which is efficiently prepared from 6-aminopenicillanic acid, e.g., by the method of Leanza et al., Tetrahedron, vol. 39, pages 2505–2513 (1983). As the first stage in a projected synthesis, the azetidinone of Leanza et al. was converted to the novel compound of the formula

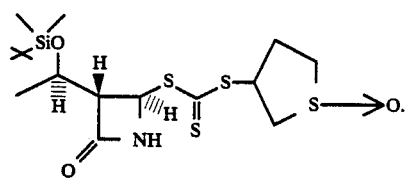

However, this compound lacked utility for subsequently proposed reaction with an acid chloride, since the latter reacted preferentially with the thiolane sulfoxide group, producing useless products. But unexpectedly, substitution of acid fluoride for acid chloride led to selective acylation on nitrogen to form previously unavailable compounds of the formula (IIIb) below, thus establishing a utility for the precursors of the formula (IIIa) below, and providing, by further transformations, further valuable intermediates of the formula (II) below. Although the above dimethyl-t-butylsilyl hydroxy protecting group is preferred, other silyl hydroxy protecting groups can, of course, be substituted therefor.

Thus, the present invention is directed to compounds of the formulae:

(a) 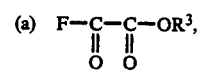

wherein $R^3$ is

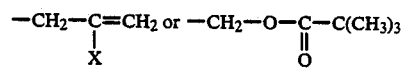

and X is hydrogen or chloro;

(b) 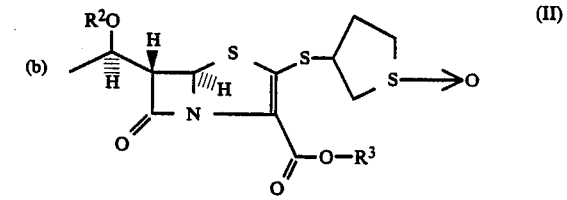
(II)

wherein $R^3$ is as defined above and $R^2$ is hydrogen or a conventional silyl hydroxy protecting group (preferably dimethyl-t-butylsilyl), with the proviso that $R^2$ is other than hydrogen when $R^3$ is pivaloyloxymethyl; and (c) 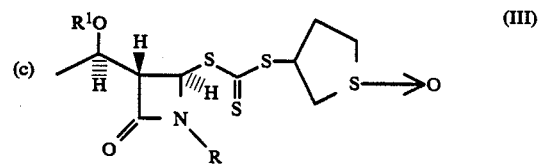
(III)

wherein $R^1$ is a conventional silyl hydroxy protecting group (preferably dimethyl-t-butylsilyl), and R is hydrogen or

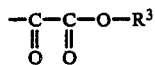

where R³ is as defined above.

Also encompassed by the present invention is a process for the preparation of a compound of the formula

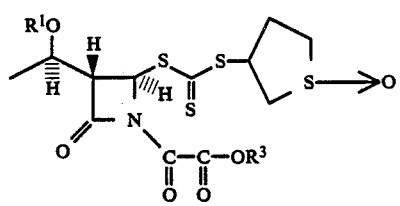
(IIIb)

wherein R¹ and R³ are as defined above, which comprises acylation of a compound of the formula

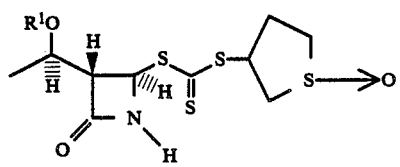
(IIIa)

with an acid fluoride of the formula

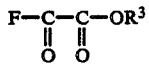
(IV)

in a reaction-inert solvent at 0° to −80° C. in the presence of a tertiary amine. Lower temperatures, e.g., −20° to −70° C., are preferred. The process further comprises conventional methods of converting the product (IIIb) to the compounds of the above formula (I) via compounds of the formula (II).

Finally, when R³ is pivaloyloxymethyl, the present invention is directed to a process for the conversion of the corresponding acid chloride to the acid fluoride (IV) using potassium fluorosulfinate as reagent.

The expression "reaction-inert solvent" defines a solvent which does not interact with reagents, intermediates or product in a manner which adversely affects the yield of the desired product.

The present invention also encompasses a process for the conversion of a compound of the above formula (II) wherein R² is hydrogen and R³ is other than pivaloyloxymethyl, to a compound of the above formula (I) or a pharmaceutically-acceptable cationic salt thereof.

Those skilled in the art will know that benzyl or p-nitrobenzyl esters could be substituted for above allyl or 2-chloroallyl esters, now with final deprotection by conventional hydrogenolysis procedures.

DETAILED DESCRIPTION OF THE INVENTION

In the first stage of the present synthesis, racemic cis- or trans-3-(acetylthio)thiolane 1-oxide is converted to the mercaptide salt by the action of an alkali metal alkoxide, such as sodium methoxide, under strictly anhydrous conditions in a reaction inert solvent such as isopropyl alcohol,

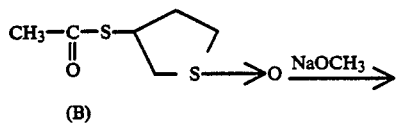
(B)

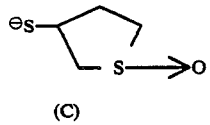
(C)

preferably at reduced temperature (e.g., −5° to −45° C.), most preferably at −20° to −30° C. Maintaining the same anhydrous and reduced temperature conditions, the mercaptide salt (C) is reacted with carbon disulfide to form the salt of the formula

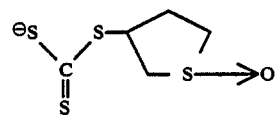
(D)

which is in turn reacted with an azetidinone such as that of the above formula (A), generally at somewhat higher temperature (e.g., −20° to 20° C.), preferably at −5° to +5° C., to form the compound of the formula (IIIa) above. Each of the resulting cis- and transproducts are composed of a pair of diastereoisomers in approximately equal quantities.

The compound of the formula (IIIa) is then reacted with the acid fluoride of the formula (IV) under conditions as generally described and summarized above. The most preferred initial temperature range is −45° to −60° C., ultimately increased to −15° to −25° C. An ideal reaction-inert solvent is methylene chloride. An ideal tertiary amine is N,N-diisopropylethylamine.

In the next stage of the synthesis, the compound of the formula (II) wherein R² is a silyl-protecting group, now containing the completed penem ring system, is formed by the action of a trialkyl phosphite (e.g., triethyl phosphite) on a compound of the formula (IIIb), in a reaction-inert solvent (e.g., ethanol-free chloroform). Temperature is not critical, but will generally be above ambient, e.g., 40° to 80° C., conveniently reflux temperature when chloroform is the solvent.

In the final or penultimate step, the silyl-protecting group is removed by standard methods, e.g., in the case of the dimethyl-t-butylsilyl, by the action of acetic acid and tetrabutylammonium fluoride in anhydrous tetrahydrofuran, to form the compound of the formula (I) in the form of its pivaloyloxymethyl ester or of the formula (II) wherein R² is hydrogen.

Finally, when R³ is allyl or 2-chloroallyl, the ester is hydrolyzed to produce the desired penem of the formula (I), above, in the form of the acid or its pharmaceutically-acceptable cationic salt. Anhydrous conditions are generally employed to avoid degradation of the beta-lactam. Preferred conditions employ 1 to 1.1 molar equivalents of an alkali metal salt of a lipophilic carboxylic acid (e.g., sodium 2-ethylhexanoate) in an anhydrous reaction-inert solvent (e.g., methylene chloride and/or ethyl acetate) in the presence of catalytic amounts of triphenylphosphine and tetrakis(triphenylphosphine)palladium (e.g., about 0.15 molar equivalents of the former and about 0.075 molar equivalents of the latter). Although temperature is not critical, the reaction is conveniently carried out at ambient temperature.

The required acid fluorides (IV) are prepared from the corresponding acid chlorides using reagents previously used for this purpose, either anhydrous cesium fluoride (usually at or near ambient temperature, with reagents initially combined at lower temperature, e.g., 0° to −30° C.), or potassium fluorosulfinate ($FSO_2K$, usually at warmer temperatures, e.g., 45°-85° C.). Surprisingly, only the latter reagent and conditions produce a satisfactory yield of the acid fluoride when $R^3$ is pivaloyloxymethyl.

Concerning the starting materials required for the process of the present invention, 3R-,4R-4-acetoxy-3-[1R-1-(silyloxy)ethyl]-2-azetidinones are readily available according to the method of Leanza et al., cited above; each of racemic cis- and trans-3-(acetylthio)thiolane 1-oxide are available according to the method of the European patent application cited above; allyl oxalochloride is available according to the method of Afonso et al., J. Am. Chem. Soc., vol. 104, pages 6138-6139 (1982); 2-chloroallyl oxalochloride is available from 2-chloroallyl alcohol and oxalyl chloride according to the method detailed below; and pivaloyloxymethyl oxalochloride is prepared by a series of steps from benzyl half ester of oxalic acid and chloromethyl pivalate, also detailed below.

The following examples are given by way of illustration and are not to be construed as limitations of this invention, many variations of which are possible within the scope and spirit thereof.

EXAMPLE 1

3S,4R-3-[1R-1-(Dimethyl-t-butylsilyloxy)ethyl]-4-[cis-1-oxo-3-thiolanylthio(thiocarbonyl)thio]-2-azetidinone A flame-dried, three-neck flask equipped with a mechanical stirrer, dropping funnel and low temperature thermometer under a $N_2$ atmosphere was charged with racemic, cis-3-(acetylthio)thiolane 1-oxide (4.26 g, 23.9 mmol) and 90 ml isopropyl alcohol. The reaction was cooled to an internal temperature of −20° C. and sodium methoxide (1.18 g, 21.9 mmol) was added in one portion. The reaction was stirred at −20° to −25° C. for ninety minutes, then allowed to warm to −10° C. The reaction was recooled to −30° C. and a solution of carbon disulfide (7.94 g, 104 mmol) in 30 ml isopropyl alcohol was added dropwise over a thirty minute period. The reaction was stirred at −25° to −30° C. for forty minutes. A solution of 3R,4R-4-acetoxy-3-[1R-1-(di-methyl-t-butylsilyloxy)ethyl]-2-azetidinone [6 g, 20.9 mmol; Leanza et al., Tetrahedron 39, pages 2505-2513 (1983)] in 54 ml isopropyl alcohol was added dropwise over a thirty-minute period. The reaction was stirred at −20° C. for thirty minutes, then allowed to warm to 0° C. and stirred at 0° to 1° C. for ninety minutes. The reaction was quenched with 150 ml saturated ammonium chloride solution, and then 200 ml ethyl acetate was added. The mixture was transferred to a separatory funnel and 150 ml brine was added. The organic layer was separated and the aqueous layer was extracted with an additional 200 ml ethyl acetate. The combined ethyl acetate extracts were washed two times with 100 ml portions brine. The organic layer was cooled to 5° C. and dried over $MgSO_4$, then filtered and concentrated in vacuo to yield a viscous oil. The oil was azeotroped four times with 50 ml portions of methylene chloride and pumped under high vacuum to yield 8.32 g (90.5%) of a yellow foam comprising a mixture of two title diastereoisomers.

An analytical sample was prepared by stirring a sample of the above foam with isopropyl ether for two hours. The yellow solids were filtered and dried, m.p. 85°-89° C. (decomposition).

Analysis calculated for $C_{16}H_{29}O_3NS_4Si$: C, 43.69; H, 6.65; N, 3.19%. Found: C, 43.41; H, 6.38; N, 3.06%.

IR(KBr) $cm^{-1}$ 1770.

$^1$H-NMR($CDCl_3$)delta(ppm): 0.072 (s, 3H, $CH_3Si$), 0.077 (s, 3H, $CH_3Si$), 0.877 (s, 9H, t-butyl), 1.21 (d, J=6.1 Hz, 3H, $CH_3$), 2.74-3.24 (m, 6H, 3 $CH_2$), 3.78 (m, 1H, CHS), 4.29 (dd, J=6.1, 3.7 Hz, 1H, CH), 4.55 (m, 1H, CHO), 5.65 (m, 1H, CHS), 6.65 (bs, 1H, NH).

EXAMPLE 2

3S,4R-N-[(2-Chloroallyloxy)oxalyl]3-[1R-1-(dimethyl-t-butylsilyloxy)ethyl]4-[cis-1-oxo-3-thiolanylthio(thiocarbonyl)thio]-2-azetidinone A flame-dried, three-neck flask equipped with a dropping funnel and low temperature thermometer under a $N_2$ atmosphere was charged with the product of the preceding Example (52.2 g, 118.7 mmol) and 975 ml dry methylene chloride (passed through neutral alumina). The reaction was cooled to −50° to −55° C. internal temperature and 2-chloroallyl oxalofluoride (24.7 g, 148.4 mmol) was added dropwise over a twenty minute period, and the reaction was stirred an additional ten minutes at −50° to −55° C. 16.1 g (124.6 mmole) N,N-diisopropylethylamine was added dropwise over a sixty-five minute period. The reaction was stirred at −50° to −55° C. for seventy-five minutes. The reaction was allowed to warm to −20° C. and slowly quenched with 900 ml $H_2O$. The organic layer was separated, washed with an additional 900 ml $H_2O$ and 900 ml brine. The organic layer was dried over $MgSO_4$, filtered and concentrated in vacuo to yield 65.6 g (94%) of a yellow foam as a mixture of two diastereoisomers.

$^1$H-NMR($CDCl_3$)delta(ppm): 0.033 (s, 3H, $CH_3Si$), 0.095 (s, 3H, $CH_3Si$), 0.86 (s, 9H, t-butyl), 1.24 (d, J=6.4 Hz, 3H, $CH_3$), 2.75-3.77 (m, 7H, thiolane), 4.43 (m, 1H, CH), 4.66 (m, 1H, CHO), 4.84 (s, 2H, $CH_2$), 5.47 (d, 1H, vinyl CH), 5.56 (d, 1H, vinyl CH), 6.7 and 6.74 (2d, J=3.7 Hz, 1H, NCHS).

IR(KBr) $cm^{-1}$ 1820, 1762, 1708.

EXAMPLE 3

2-Chloroallyl 5-R,6S-6-[1R-1-(Dimethyl-t-butylsilyloxy)ethyl]-2-(cis-1-oxo-3-thiolanylthio)-2-penem-3-carboxylate A flame-dried, three-neck flask equipped with a condenser and an equilibrating addition funnel under a $N_2$ atmosphere was charged with the product of the preceding Example (15.6 g, 26.6 mmol) and 800 ml ethanol-free chloroform. The reaction was heated to a gentle reflux and triethyl phosphite (9.3 g, 56 mmol) in 70 ml ethanol-free chloroform was added dropwise over an eight hour period. The reaction was heated at a gentle reflux for an additional eight hours. The reaction was cooled to room temperature and concentrated in vacuo. The residue was stirred with cold isopropyl ether, filtered and dried to yield 6.23 g (43%) of an off-white solid as a mixture of two diastereoisomers; m.p. 138°-140° C.

Analysis calculated for $C_{21}H_{32}O_5NS_3ClSi$: C, 46.86; H, 5.99; N, 2.60; S, 17.87%. Found: C, 46.71; H, 5.94; N, 2.49; S, 17.73%. $^1$H-NMR($CDCl_3$)delta(ppm): 0.064 (s, 6H, 2CH₃Si), 0.87 (s, 9H, t-butyl), 1.24 (d, J=6.4 Hz, 3H, CH₃), 2.70–4.05 (m, 8H, CHCO, thiolane), 4.25 (m, 1H, CH), 4.74 (q, $J_{AB}$=14.1 Hz, 2H, CH₂), 5.38 (d, J=0.5 Hz, 1H, CHS), 5.66 (m, 2H, vinyl CH₂).

IR(KBr)cm⁻¹ 1784.

EXAMPLE 4

2-Chloroallyl 5R,6S-6-(1R-1-Hydroxyethyl)-2-(cis-1-oxo-3-thiolanyl-thio)-2-penem-3-carboxylate A flame-dried, three-neck flask equipped with a thermometer and two addition funnels under a N₂ atmosphere was charged with the product of the preceding Example (22.7 g, 42 mmol) and 65 ml dry tetrahydrofuran. The reaction was cooled to an internal temperature of 5° C. and 25.2 g (420 mmol) of glacial acetic acid was added dropwise over a fifteen minute period keeping the internal temperature at 5° C. Tetrabutyl ammonium fluoride in tetrahydrofuran (1M, 126 ml) was added dropwise over a one hour period keeping the internal temperature at 5° C. The reaction was allowed to slowly warm to room temperature and stirred an additional sixteen hours at room temperature. The reaction was poured into 2000 ml iced H₂O and extracted 3×1000 ml ethyl acetate. The combined organic extracts were washed 3× 650 ml H₂O, 2× 650 ml saturated NaHCO₃ and 2× 650 ml brine, dried over Na₂SO₄, filtered and concentrated in vacuo to yield 14.14 g (79%) of a yellow solid as a mixture of two diastereoisomers. A standard sample was prepared by triturating a portion of the sample in ethyl acetate; m.p. 145°–149° C. (decomposition).

¹H-NMR(DMSO-d₆)delta (ppm): 1.17 (d, J=6.8 Hz, 3H, CH₃), 2.38–4.04 (m, 9H, CHCO, CHO, thiolane), 4.78 (q, $J_{AB}$=14.1 Hz, 2H, CH₂), 5.25 (d, J=4.4 Hz, 1H, OH), 5.48 (s, 1H, CHS), 5.76 (d, 2H, vinyl CH₂).

IR(KBr) cm⁻¹ 1769.

Analysis calculated for C₁₅H₁₈O$_N$S₃Cl: C, 42.49; H, 4.28; N, 3.31%. Found: C, 42.79; H, 4.39; N, 3.28%.

EXAMPLE 5

Sodium 5R,6S-6-(1R-1-Hydroxyethyl)-2-(cis-1-oxo-3-thiolanyl-thio)-2-penem-3-carboxylate A flame dried flask wrapped in aluminum foil under an argon atmosphere was charged with the product of the preceding Example (18.2 g, 43 mmol) in 400 ml of degassed CH₂Cl₂, triphenylphosphine (1.69 g, 6.5 mmol), sodium 2-ethylhexanoate (60.1 ml of 0.82M in ethyl acetate, 49 mmol) and tetrakis(triphenylphosphine)palladium (3.69 g, 3.2 mmol). The reaction was stirred at room temperature for seventy minutes, an additional 350 mg tetrakis(triphenylphosphine)palladium was added and the reaction stirred at room temperature an additional twenty-five minutes. Degassed ethyl acetate (275 ml) was added to the reaction over a six minute period. The reaction was stirred at room temperature for thirty minutes, filtered and the solids briefly air-dried, then slurried with 180 ml acetone for thirty minutes, filtered and dried to afford the 15.3 g (97%) of product as a yellow solid as a mixture of two diastereoisomers, corresponding to the cis-1-oxo-3-thiolanyl isomer of Example 2, page 20 of European Patent Application No. 130,025.

By the same method, the product of Example 9, below, is converted to the same title product in similar yield.

EXAMPLE 6

5R,6S-6-(1R-1-Hydroxyethyl)-2-(cis-1-oxo-3-thiolanyl-thio)-2-penem-3-carboxylic Acid The sodium salt of the preceding Example (1 g) was dissolved in 10 ml H₂O and extracted 3× 3 ml butanol and then 2× 3 ml ethyl acetate. The aqueous was stirred at 0°–5° C. with 750 mg activated carbon for forty-five minutes, then filtered. The filtrate was extracted 3× 3 ml butanol, then 2× 3 ml ethyl acetate. The aqueous was stirred at 0°–5° C. with 750 mg activated carbon for ninety minutes, then filtered and freeze-dried to yield 696 mg of a pale tan solid. The latter was dissolved in 1.2 ml H₂O, cooled to 0°–5° C., acidified to pH 2.6 with 1N HCl, stirred at 0°–5° C. for forty-five minutes, filtered, washed with a small amount of H₂O and dried to yield 374 mg of a white solid, a mixture of two diastereoisomers; m.p. 178°–181° C. (decomposition).

IR(KBr) cm⁻¹ 1778, 1745.

¹H-NMR(DMSO-d₆) delta(ppm): 1.16 (d, J=5.6 Hz, 3H, CH₃), 2.38–4.00 (m, 9H, CHCO, CHO, thiolane), 5.25 (bs, 1H, OH), 5.72 (s, 1H, CHS).

Analysis calculated fo C₁₂H₁₅O₅NS₃: C, 41.24; H, 4.33; N, 4.01%. Found: C, 41.32; H, 4.24; N, 3.82%.

EXAMPLE 7

3S,4R-N-(Allyloxyoxalyl)-3-[1R-1-(dimethyl-t-butyl-silyloxy)ethyl]-4-[cis-1-oxo-3-thiolanylthio(thiocarbonyl)thio]-2-azetidinone Except that the reaction mixture was maintained at −50° C. for 3.5 hours and not warmed to −20° C. prior to quenching, the procedure of Example 2 was employed to react the title product of Example 1 (1.00 g, 0.00227 mol) with allyl oxalofluoride (0.37 g, 0.00283 mol) to yield present title product ss a viscous yellow oil, 1.19 g.

¹H-NMR(CDCl₃)300 MHz delta: 0.04 (s, 3H), 0.10 (s, 3H), 0.86 (s, 9H), 1.24 (d, 3H, J=6.3 Hz), 2.74 (m, 3H), 2.84 (m, 1H), 3.17 (m, 1H), 3.58 (m, 1H), 3.79 (dd, 1H, J=8.8, 14.7 Hz), 4.40 (m, 1H), 4.79 (d, 2H, J=5.9 Hz), 5.32 (dd, 1H, J=1, 10.5 Hz), 540 (dd, 1H, J=1, 17.2 Hz), 5.94 (ddt, 1H, J=5.9, 10.5, 17.2 Hz), 6.70 and 6.72 (2d, 1H, J=3.5 Hz).

EXAMPLE 8

Allyl 5R,6S-6-[1R-1-(Dimethyl-t-butylsilyloxy)ethyl]-2-(cis-1-oxo-3-thiolanylthio)-2-penem-3-carboxylate By the procedure of Example 3, the product of the preceding Example (1.19 g, 0.00216 mol) was converted to present title product, triturated with pentane rather than isopropyl ether, 0.73 g, which was further purified by silica gel chromatography with ethyl acetate as eluant, 0.415 g; tlc Rf 0.3 (ethyl acetate). ¹H-NMR(CDCl₃)300 MHz delta: 0.08 (s, 6H), 0.88 (s, 9H), 1.25 (d, 3H, J=6.3 Hz), 2.6–2.9 (m, 4H), 3.13 (m, 1H), 3.64 (m, 1H), 3.70 and 3.72 (2dd, 1H, J=1.5, 4.7 Hz), 3.84 and 3.97 (2dd, 1H, J=8.4, 14.2 Hz), 4.24 (m, 1H), 4.70 (m, 2H), 5.24 (dd, 1H, J=1.3, 10.5 Hz), 5.40 (dd, 1H, J=1.3, 17.1 Hz), 5.63 and 5.65 (2d, 1 H, J=1.5 Hz), 5.93 (ddt, 1 H, J=5.6, 10.5, 17.1 Hz).

EXAMPLE 9

Allyl 5R,6S-6-(1R-1-Hydroxyethyl)-2-(cis-1-oxo-3-thiolanyl-thio)-2-penem-3-carboxylate By the procedure of Example 4, the product of the preceding Example (200 mg, 0.397 mmol) was converted to present title product, purified by chromatography on silica gel with 1:19 $CH_3OH$:ethyl acetate as eluant, 133 mg.

$^1$H-NMR($CDCl_3$)300 MHz: 1.36 (d, 3H, J=6.2 Hz), 2.46 and 2.51 (2 br d, 1H), 2.6–2.9 (m, 4H), 3.14 (m, 1H), 3.6–3.8 (m, 2H), 3.81 and 3.93 (2dd, 1H, J=8, 14 Hz), 4.23 (m, 1H), 4.66 (dd, 1H, J=5.6, 13 Hz), 4.77 (dd, 1H, J=5.6, 13 Hz), 5.25 (d, 1H, J=10.5 Hz), 5.41 (d, 1H, J=17.1 Hz), 5.67 and 5.70 (2s, 1H), 5.94 (ddt, 1H, J=5.6, 10.5, 17.1).

IR(KBr) $cm^{-1}$ 3233, 1767, 1681, 1495, 1316, 1201, 1124.

EXAMPLE 10

3S,4R-N-(Pivaloyloxymethyloxyoxalyl)-3-[1R-1-(dimethyl-t-butylsilyloxy)ethyl]-4-[cis-1-oxo-3-thiolanylthio(thiocarbonyl)thio]-2-azetidinone The product of Example 1 (4.65 g, 0.0106 mol) was dissolved in 21.1 ml dried $CH_2Cl_2$ and cooled to $-30°$ C. Pivaloyloxymethyl oxalofluoride (4.36 g, 0.0211 mol) was added and the mixture cooled to $-50°$ C. N,N-diisopropylethylamine (1.63 g, 2.21 ml, 0.0127 mol) was added via syringe over 5 minutes, during which the reaction exothermed to $-35°$ C. After 35 minutes at $-35°$ to $-50°$ C., the mixture was diluted with 125 ml dry $CH_2Cl_2$ and then with 185 ml $H_2O$. The $CH_2Cl$ layer was separated, washed 1× 185 ml fresh $H_2O$, dried over $Na_2SO_4$ and stripped to yield title product, 7.06 g; contaminated with acid fluoride, but of adequate purity for the next step; tlc Rf 0.3 (ethyl acetate).

$^1$H-NMR($CDCl_3$, 90 MHz)delta(ppm): 0.04 (s, 3H), 0.10 (s, 3H), 0.88 (s, 9H), 1.21 and 1.2–1.6 (s and m, 12H), 2.6–3.4 (m, 5H), 3.6–4 (m, 2H), 4.4–4.8 (m, 2H), 5.85 (s, 2H), 7.2 (m, 1H).

EXAMPLE 11

Pivaloyloxymethyl 5R,6S-6-[1R-1-(Dimethyl-t-butylsilyloxy)ethyl]-2-(cis-1-oxo-3-thiolanyl-thio)-2-penem-3-carboxylate By the procedure of Example 3, the product of the preceding Example (6.98 g crude, 6.52 g corrected, 0.0104 mol) was converted to present crude title product (11.8 g), which, without titration, was further purified by taking up in 480 ml hexane and 90 ml $CH_2Cl_2$, washing 4× 300 ml $H_2O$, drying over $Na_2SO_4$ and stripping to a golden oil (8.71 g), still having the odor of triethyl phosphite. Crystallization of the latter from ethyl acetate (12 ml used to dissolve) and hexane (165 ml to the cloud point, 300 ml more during digesting for 3 hours) gave purified title product, 2.50 g; tlc Rf 0.15 (ethyl acetate).

$^1$H-NMR($CDCl_3$)delta(ppm): 0.1 (s, 6H), 0.9 (s, 9H), 1.2 (m, 12H), 2.4–4.5 (m, 9H), 5.7 (dd, 1H), 5.9 (q, 2H).

EXAMPLE 12

Pivaloyloxymethyl 5R,6S-6-(1R-1-Hydroxyethyl)-2-(cis-1-oxo-3-thiolanyl-thio)-2-penem-3-carboxylate By the procedure of Example 4, the product of the preceding Example (1.88 g, 3.25 mmol) was converted to present title product initially isolated by diluting the reaction mixture with 500 ml ethyl acetate, washing with 3× 150 ml brine, drying over $Na_2SO_4$ and stripping. The resulting residue was redissolved 200 ml ethyl acetate, washed 2× 150 ml $H_2O$ each time adding sufficient brine to break the emulsion, and the combined aqueous extracts backwashed with ethyl acetate and combined with the original organic layer. The latter combination was dried over $Na_2SO_4$ and restripped to a foam, 1.66 g, which was crystallized from ethyl acetate and ether to yield purified title product, 1.34 g; ir(KBr) 2.96, 5.60, 5.69, 5.91 and 6.75 microns.

$^1$H-NMR($CDCl_3$, 250 MHz)delta(ppm): 1.23 (s, 9H), 1.35 (d, 3H), 2.5 (bc, 1H), 2.6–2.9 (c, 4H), 3.16 (m, 1H), 3.62–4.0 (c, 3H), 4.25 (m, 1H), 5.7 and 5.72 (2d, 1H), 5.88 (q, 2H).

PREPARATION 1

2-Chloroallyl Oxalofluoride [(2-Chloroallyloxy)oxalyl Fluoride]$CH_2$=$CClCH_2O(CO)COF$ Under dry $N_2$ in flame dried glass apparatus, cesium fluoride (167 g, 1.1 mol) was placed in a 1 liter single neck flask and placed under high vacuum and gently heated with a flame until the solid became free flowing, then cooled to room temperature. Acetonitrile, distilled from $CaH_2$ (183 ml) was added and the mixture cooled to $-20°$ C. internal temperature. 2-Chloroallyl oxalochloride (183 g, 1.0 mol) was added dropwise over a 30 minute period and the mixture slowly warmed to room temperature, stirred at that temperature for 16 hours, and byproduct cesium chloride recovered by filtration with acetonitrile wash. The filtrate and wash were combined and stripped, and the residue distilled at reduced temperature to yield 129 g (77%) of the desired product, b.p. $62°–64°$ C./22 mm.

IR($CHCl_3$) $cm^{-1}$ 1770, 1870.

$^1$H-NMR($CDCl_3$)delta(ppm) 4.80 (s, 2H), 5.4–5.6 (m, 2H).

PREPARATION 2

Allyl Oxalofluoride [Allyloxalyl Fluoride]$CH_2$=$CHCH_2O(CO)COF$

By the procedure of the preceding Prepration, allyl oxalochloride (252.5 g, 1.70 mol) and cesium fluoride (284 g, 1.87 mol) were converted to twice distilled title product, b.p. $48°–50°$ C./35 mm; $124°–126°$ C. (atmospheric pressure).

$^1$H-NMR($CDCl_3$)250 $MH_3$, delta: 4.76 (d, 2H, J=6 Hz), 5.28 (dd, 1H, J=1, 17 Hz), 5.37 (dd, 1H, J=1, 17 Hz), 5.90 (ddt, 1H, J=6, 11, 17 Hz).

$^{13}$C-NMR($CDCl_3$)63 MHz, delta: 68.5 (t), 120.4 (t), 129.7 (d), 146.3 (d, $J_{C-F}$=375 Hz), 153.0 (d, $J_{C-C-F}$=87 Hz). IR(neat) 1860 (C=O), 1770 (C=O), 1120 $cm^{-1}$.

PREPARATION 3

[2-Chloroallyl Oxalochloride [(2-Chloroallyloxy)oxalyl Chloride]

Oxalyl chloride (130 ml, 1.49 mol) was placed in a dry 3-neck flask under $N_2$ and cooled to 0° C. With stirring, 2-chloroallyl alcohol (138 g, 1.49 mol) was added dropwise in a manner which maintained the temperature at 0°-2° C. and controlled the vigorous evolution of HCl, then allowed to warm to room temperature and held 16 hours and distilled to yield title product, 214 g, b.p. 82°-84° C./23 mm.

PREPARATION 4

Benzyl Oxalochloride [(Benzyloxy)oxalyl Chloride]

Under $N_2$, oxalyl chloride (262 ml) was dissolved in 1 liter anhydrous ether and heated to reflux, at which temperature benzyl alcohol (207 ml) was added over 70 minutes. After refluxing a further 16 hours, ether was stripped and the residue distilled at reduced pressure to yield 372 g (94%) of title product, b.p./0.7 mm 85° C.

PREPARATION 5

Oxalic Acid, Half Benzyl Ester

Title product of the preceding Preparation (180 g, 0.91 mol) in 800 ml ether was cooled in an acetone-dry ice bath. As the mixture was allowed to warm to 0° C., aqueous $NH_4OH$ (2M, 906 ml, 0.91 mol) was added portionwise. The mixture was then warmed to room temperature, stirred 1 hour, and the pH adjusted to 8.5 with 95 ml 2M $NH_4OH$. The aqueous layer was separated, extracted 2× 400 ml ether, layered with 500 ml fresh ether, cooled to 10° C. and the pH adjusted to 1.5 with 2M HCl. The layers were separated, the aqueous layer extracted 2× 400 ml ether, and the three acidic organic layers combined, washed with 500 ml brine, dried over $Na_2SO_4$ and stripped to yield title product as white solids, 163 g. $^1$H-NMR(CDCl$_3$)delta(ppm): 5.2 (s, 1H), 6.95 (s, 2H), 7.3 (s, 5H).

PREPARATION 6

Benzyl Pivaloyloxymethyl Oxalate

The product of the preceding Preparation (163 g, 0.91 mol) was dissolved in 1 liter CHCl$_3$ and carefully neutralized (foaming) with NaHCO$_3$ (76.2 g, 0.91 mol). Separately, tetrabutylammonium hydrogen sulfate (308 g, 0.91 mol) in 1.5 liters H$_2$O was carefully neutralized with a like quantity of NaHCO$_3$. The former slurry was added slowly to the latter solution, the mixture stirred vigorously for 20 minutes, the aqueous layer separated and washed with 500 ml fresh CHCl$_3$. The organic layers were combined, dried over Na$_2$SO$_4$ and stripped to yield tetrabutylammonium benzyl oxalate, 478 g. The latter was taken up in 400 ml acetone. Chloromethyl pivalate (118 ml, 0.82 mol) was added and the mixture stirred under N$_2$ for 16 hours at ambient temperature. The acetone was stripped, and the residue taken up in 1 liter ethyl acetate, washed 4× 500 ml H$_2$O and 1× 500 ml brine, dried over Na$_2$SO$_4$ and stripped to yield title product as an oil, 201 g; tlc Rf 0.60 (2:3 ethyl acetate:-hexane).

$^1$H-NMR(CDCl$_3$, 90 MHz)delta(ppm): 1.21 (s, 9H), 5.2 (s, 2H), 5.8 (s, 2H), 7.3 (s, 5H).

PREPARATION 7

Oxalic Acid, Half Pivaloyloxymethyl Ester

Title product of the preceding Preparation (27.3 g, 0.093 mol) and 2.8 g of 10% Pd/C were combined in 150 ml ethyl acetate and hydrogenated in a Paar hydrogenation apparatus at 4× atmospheric pressure and ambient temperature for 1.5 hours. The catalyst was recovered by filtration over diatomaceous earth and the filtrate stripped to yield title product as an oil, 19.3 g.

$^1$H-NMR(CDCl$_3$, 90 MHz)delta(ppm): 1.21 (s, 9H), 5.96 (s, 2H), 10.31 (s, 1H).

PREPARATION 8

Pivaloyloxymethyl Oxalochloride

Title product of the preceding Preparation (19.2 g, 0.094 mol) was dissolved in 20 ml benzene and added portionwise over 20 minutes to oxalyl chloride (47.7 g, 33 ml, 0.376 mol) in 100 ml benzene. After 30 minutes, the mixture was stripped and the residue (19.2 g) distilled to yield title product, 16.4 g; b.p. 83° C./0.4 mm.

PREPARATION 9

Pivaloyloxymethyl Oxalofluoride [Pivaloyloxymethyloxalyl Fluoride](CH$_3$)$_3$C(CO)OCH$_2$O(CO)COF Potassium fluorosulfinate (80% KSO$_2$F, 2.40 g, 1.92 g corrected, 0.016 mol) was added to oxalyl chloride (3.50 g, 0.016 mol) and the mixture gradually warmed in an oil bath to 60° C., at which point vigorous gas evolution began. The bath was removed. Once the reaction subsided, the oil bath was replaced, the mixture warmed to 80° C. and held for 15 minutes, cooled to 60° C. and distilled from a bath at 60° C. to yield title product, 1.19 g; b.p. 52°-54° C./0.4 mm.; solidified on storage at −50° C., melts at ambient temperature.

$^{13}$C-NMR: 176.6, 152.6 and 151.5, 148.1 and 140.2, 81.7, 38.8, and 26.6, with splitting of oxalate carbonyls 89 Hz and 252.6 Hz.

We claim:

1. A compound of the formula

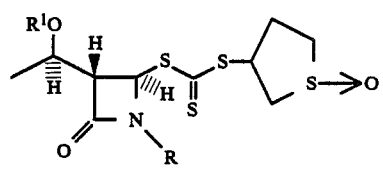

(III)

wherein R is hydrogen or

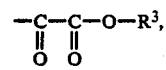

$R^3$ is

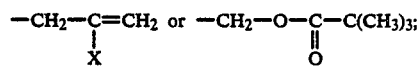

X is hydrogen or chloro; and
$R^1$ is

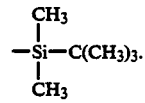

2. A compound of claim 1 wherein the group attached to the thiolane ring possesses cis relative stereochemistry.

3. A compound of claim 2 wherein R is hydrogen.

4. A compound of claim 2 wherein R is

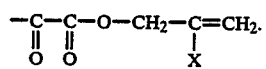
5. The compound of claim 2 wherein R is
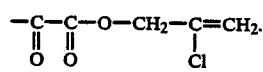
6. The compound of claim 2 wherein R is
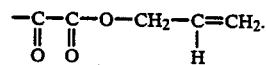
7. The compound of claim 2 wherein R is
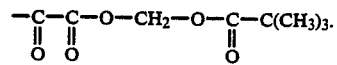
* * * * *